(12) United States Patent
Prikoszovich

(10) Patent No.: US 6,353,030 B1
(45) Date of Patent: Mar. 5, 2002

(54) RELATING TO ORGANIC COMPOUNDS

(75) Inventor: Walter Prikoszovich, Schönenbuch (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/089,836

(22) Filed: Jun. 3, 1998

Related U.S. Application Data

(63) Continuation of application No. 08/471,053, filed on Jun. 6, 1995, which is a continuation of application No. 08/353,467, filed on Dec. 9, 1994, which is a continuation of application No. 08/121,674, filed on Sep. 15, 1993, which is a continuation of application No. 07/737,091, filed on Jul. 30, 1991.

(30) Foreign Application Priority Data

Aug. 1, 1990 (GB) .............................................. 9016840
Aug. 1, 1990 (GB) .............................................. 9016882

(51) Int. Cl.⁷ ......................... A61K 47/34; C08G 63/85
(52) U.S. Cl. ................................ 514/772.1; 514/772.7; 528/357
(58) Field of Search ................................. 424/486, 426, 424/428; 514/772.1, 772.7; 528/357

(56) References Cited

U.S. PATENT DOCUMENTS

| | | |
|---|---|---|
| 2,703,316 A | 3/1955 | Schneider |
| 3,169,945 A | 2/1965 | Hostettler et al. |
| 3,755,558 A | 8/1973 | Scribner |
| 3,773,919 A | 11/1973 | Boswell et al. |
| 3,887,699 A | 6/1975 | Yolles |
| 3,933,071 A | 1/1976 | Higuchi et al. |
| 3,963,699 A | 6/1976 | Rizzi et al. |
| 3,981,303 A | 9/1976 | Higuchi et al. |
| 3,986,510 A | 10/1976 | Higuchi et al. |
| 4,001,388 A | 1/1977 | Shell |
| 4,011,312 A | 3/1977 | Reuter et al. |
| 4,033,938 A | 7/1977 | Augurt et al. |
| 4,104,464 A | 8/1978 | James |
| 4,130,639 A | 12/1978 | Shalaby et al. |
| 4,165,432 A | 8/1979 | Preston et al. |
| 4,234,571 A | 11/1980 | Nestor et al. |
| 4,243,775 A | 1/1981 | Rosensaft et al. |
| 4,273,920 A | 6/1981 | Nevin |
| 4,334,061 A | 6/1982 | Bossier, III |
| 4,379,138 A | 4/1983 | Pitt et al. |
| 4,419,340 A | 12/1983 | Yolles |
| 4,451,452 A | 5/1984 | Deibig et al. |
| 4,452,973 A | 6/1984 | Casey et al. |
| 4,526,938 A | 7/1985 | Churchill et al. |
| 4,529,736 A | 7/1985 | McKenzie et al. |
| 4,585,651 A | 4/1986 | Beck et al. |
| 4,675,189 A | 6/1987 | Kent et al. |
| 4,756,907 A | 7/1988 | Beck et al. |
| 4,874,612 A | 10/1989 | Beasy |
| 4,891,263 A | 1/1990 | Kotliar et al. |
| 4,920,203 A | 4/1990 | Tang et al. |
| 4,960,866 A | * 10/1990 | Bendix et al. |
| 4,983,745 A | 1/1991 | Muller et al. |
| 5,053,485 A | 10/1991 | Nieuwenhuis et al. |
| 5,672,659 A | * 9/1997 | Shalaby et al. |

FOREIGN PATENT DOCUMENTS

| | | |
|---|---|---|
| EP | 0025698 | 6/1984 |
| EP | 0026599 | 6/1984 |
| EP | 0021234 | 8/1984 |
| EP | 0058481 | 10/1986 |
| EP | 0092918 B1 | 10/1988 |
| EP | 0 368 571 A2 | 5/1990 |
| EP | 0 452 111 A2 | 10/1991 |
| EP | 0052510 B2 | 10/1994 |
| GB | 1332505 | 10/1973 |
| GB | 2008135 A | 5/1979 |

OTHER PUBLICATIONS

Jackanicz, et al., Polylactic Acid as a Biodegradable Carrier for Contraceptive Steroids—vol. 8, No. 3—pp. 227–234.
Anderson, et al., Contraception—An Injectable Sustained Release Fertility Control System—vol. 13, No. 3—Mar. 1976—pp. 375–384.
Sinclair, Environmental Science & Technology—vol. 7, No. 10—Oct. 1973—pp. 955–956.
Beck, et al., Acta Europae Fertilitatis, vol. 11, No. 2—Jun. 1980—pp. 139–150.
Yolles, et al., Bulletin of the Parenteral Drug Association—vol. 30, No. 6—Nov.–Dec. 1976—pp. 306–313.
Wise, Chemical Abstracts, vol. 91—Jul. 2, 1979—p. 275.
Schindler, et al., Journal of Polymer Science: Polymer Chemistry Ed., vol. 20, pp. 319–326 (1982).
Kricheldorf, et al., Polylacrones, Polymer Bulletin 14, 497–502, 1985.
Nemark, et al., J Polymer Science, 19, 1329–1336, 1981.
Patent Abstracts of Japan, Publication No. 61111326, May 29, 1986.
D. H. Lewis, et al., Sustained Release of Antibiotics from Biodegradable Microcapsules, Southern Research Institute, Birmingham, Alabama—1980—pp. 129–131.
Chang, Journal of Bioengineering—vol. 1—1976—pp. 25–32.
Frazza, et al., Journal of Biomedical Materials Research—vol. 5, No. 1—Jan. 1971—pp. 43–58.
Miller, et al., J. Biomed. Mater. Res.—vol. 11—1977—pp. 711–719.

(List continued on next page.)

*Primary Examiner*—Edward J. Webman
(74) *Attorney, Agent, or Firm*—Hesna J. Pfeiffer

(57) ABSTRACT

A polylactide in a purified state, which meets the requirements of
 the color strengths of reference solutions $B_2$–$B_9$ of the brown color test of the European Pharmacopoeia, 2nd Edition (1980) part I, Section V, 6.2 and
 containing one or more metals in cationic form, the metal ion(s) having a concentration of at most 10 ppm.
The polylactide is especially suitable for use as microparticles or implants, and contains preferably a hydrophilic drug, like octreotide or a lipophilic drug like bromocriptine.

4 Claims, No Drawings

OTHER PUBLICATIONS

Kulkarni, et al., J. Biomed. Mater. Res.—vol. 5—1971—pp. 169–181.
Brady, et al., J. Biomed. Mater. Res.—vol. 7—1973—pp. 155–167.
Sidman, et al., Journal of Membrane Science, vol. 7—1980—pp. 277–291.
Langer, et al., Journal of Membrane Science, vol. 7—1980—pp. 333–351.
Cutright, et al., Journal of Oral Medicine, vol. 30, No. 1—Jan.–Mar. 1975—pp. 5–7.
Wise, et al., J. Pharm. Pharmac., vol. 30—1978—pp 686–689.
Wise, et al., J. Pharm. Pharmacol.—vol. 32—1980—pp. 399–403.
Pitt, et al., Journal of Pharmaceutical Sciences—vol. 68, No. 12—Dec. 1979—pp. 1534–1538.
Schindler, et al., Journal of Polymer Science—vol. 17—1979—pp. 2593–2599.
Benagiano, et al., Journal of Steroid Biochemistry—vol. 11—1979—pp. 449–455.
Nash, et al., Journal of Steroid Biochemistry—vol. 6—1975—pp. 909–915.
Schwope, et al., Life Sciences—vol. 17—1975—pp. 1877–1885.
Kricheldorf—Makromol. Chem. Suppl. 12—1985—pp. 25–38.
Wise, et al., Midland Macromolecular Monographs—1978—pp. 121–139.
Wise, et al., Midland Macromolecular Monographs—vol. 5—1978—pp. 75–89.
Cutright, et al., Oral Sur. Oral Med. Oral Pathol—vol. 37, No. 1—1974—pp. 142–152.
Mason, Org. Coat. Plast. Chem., vol. 42—1980—pp. 436–440.
Lee, Pharmacy International—Aug. 1986—6 pages.
Gilding, et al., Polymer, vol. 20—Dec. 1979—pp. 1459–1464.
Schindler, et al., Polymer Science, vol. 2—1977—pp. 251–289.
Beck, et al., Research Frontiers in Fertility Regulation—vol. 1, No. 1—Jul. 1980, pp. 1–16.
Schwope, et al., Research Monograph Series, The National Institute on Drug Abuse, vol. 4—Jan. 1976—pp. 13–18.
Gregory, et al., Continued Development of an Implantable Sustained Release System for the Prevention of Malaria, U.S. Army Contract No. DAMD 17–74–C–4120—65 pages.
Wise, et al., G. Gregoriadis (editor), Drug Carriers in Biology and Medicine—1979—pp. 237–270.
Hydrolic Degradation of Poly DL–(Lactide)—2 pages.
Polyesters, Korshak & Vinogradove, Pergammon—1965—pp. 214–217.
Wise, et al., Sustained Delivery of a Narcotic Antagonist from Lactic/Glycolic Acid Copolymer Implants—1978—pp. 75–89.
Pitt, et al., Drug Delivery Systems, NIH Bethesda—1977—pp. 141–192.
Schindler, et al. in Contemporary Topics in Polymer Science, Biodegradable Polymers for Sustained Drug Delivery, vol. 2—1977.

* cited by examiner

RELATING TO ORGANIC COMPOUNDS

The instant application is a continuation of U.S. Ser. No. 08/471,053, filed Jun. 6, 1995, which in turn was a continuation of U.S. Ser. No. 08/353,467, filed Dec. 9, 1994, which in turn was a continuation of U.S. Ser. No. 08/121,674, filed Sep. 15, 1993, which in turn was a Continuation of U.S. Ser. No. 07/737,091, filed Jul. 30, 1991. All of these parent applications have been abandoned.

This invention relates to polylactides in a purified state, to the method of their purification and to pharmaceutical compositions comprising the purified polylactides.

The European Patent Application No. 0270987 A2 describes polylactides, e.g. polylactide-co-glycolides, which have been prepared by condensation of lactic acid and glycolic acid or preferably by polymerisation of lactide and glycolide in the presence of a catalyst, e.g. tin di-(2-ethyl hexanoate), also known as tin octoate or tin octanoate.

The polylactides are purified by dissolving them in a solvent, which is not or is only partially miscible with water, e.g. methylene chloride, and washing the solution with an aqueous solution of an acid, e.g. HCl or of a metal ion complexing agent e.g. EDTA, after which the catalyst metal cation or its complex is transferred to the aqueous solution, in which it is better soluble.

However, after separation and isolation of the organic solvent layer and the precipitation of the polylactide from it e.g. by mixing the layer with an organic solvent, e.g. petrol ether or an alcohol, e.g. methanol, which dislodges the polylactide from the solution, the precipitated polylactide still contains a certain amount of the catalyst metal cation—about 2 ppm—and additionally the catalyst anion, e.g. in acid form. Further the polylactide contains a certain amount of brown coloured decomposition by-products which have been formed in the polymer preparation process, especially under the influence of the catalyst.

Since polylactides, e.g. polylactide-co-glycolides, are preferably used as matrices for drug compounds e.g. in implants or microparticles, which are administered parenterally, the remaining impurities can give rise to local irritation reactions of the body tissue and, e.g. depending on the catalyst type, to an instability of the matrix and thus possibly to an accelerated drug compound release. The brown impurities and the catalyst should thus preferably be removed as good as possible.

Catalyst-free polylactides on the basis of the condensation of lactid acid and optionally glycolic acid are known, but have low molecular weights of about 2000 to 4000.

Polylactides of a higher molecular weight are preferred and can only be made in the presence of a catalyst.

According to the European Patent No 0026599 B1 lactic acid and glycolic acid were reacted in the presence of a strong acid ion-exchange resin as a catalyst, which after the reaction could be removed from the copolymer product by filtering the molten reaction mixture or by cooling the reaction mixture, dissolving the copolymer in an organic solvent in which the ion-exchange resin is insoluble, filtering the solution and removing the organic solvent after which a copolymer was obtained from which the solid phase catalyst was removed to a substantially extent.

However, by this method only polylactides were obtained having a molecular weight of from about 6000 to 35000.

Polylactides, e.g. polylactide-co-glycolides, having a broader molecular weight range than up to 35000 are preferably made by using lactide and optionally e.g. glycolide as monomers, but are polymerised in the presence of a metal catalyst, which reaction type, as has been discussed before, leads to a considerable contamination of the reaction product.

We have found now, that polylactides, e.g. polylactide-co-glycolides, especially those prepared from lactide and glycolide as monomers, can be obtained in a better purified state. The invention provides a polylactide in a purified state which meets the requirements of the colour strengths of reference solutions $B_2$–$B_9$ of the brown colour test of the European Pharmacopoeia, 2nd Edition (1980), part I, Section V, 6.2. and containing one or more metals in cationic form, the metal ion(s) having a concentration of at most 10 ppm.

The polylactide preferably has the reduced colour strengths of the reference solutions $B_4$–$B_9$, especially of reference solution $B_9$. The colour of a reference solution $B_9$ indicates that the polylactide is an off-white or colourless product.

The polylactides which are preferably prepared contain particularly bivalent metal ions, like $Zn^{++}$ and especially $Sn^{++}$.

For the determination of the tin amount, the polymer is decomposed under high pressure with a mixture of hydrochloric acid and nitric acid. The precipitation and concentration of tin from that mixture occurs on a membrane filter and the measurement of the metal amount is carried out by energy dispersive X-ray fluorescence (EDXRF), as described by H. D. Seltner, H. R. Lindner and B. Schreiber, Intern. J. Environ. Anal. Chem., 1981, Vol. 10, pp. 7–12 supplemented with a reference graphite furnace atomic absorption spectrometry method, as discussed on the 6th Colloquim Atomspektrometrische Spurenanalytik, Apr. 8–12th, 1991 in Konstanz, Germany, Authors: H. Seltner, G. Hermann and C. Heppler.

According to the invention the concentration of $Sn^{++}$ in the purified polyactide of the invention is preferably at most 1.5 ppm, particularly at most 1 ppm; the catalyst anion is preferably ethyl-hexanoate, which is in the purified polylactide of the invention preferably present in a concentration of at most 0.5% by weight of the polylactide.

The purified polylactide preferably contains apart from its lactide units further structural units e.g. such as described in the european Patent Application No 0270987, second passage on page 4, of which the glycolide unit is the preferred unit since, depending on its monomer ratio in the polymer chain, it can shorten the decomposition period of the polymer in the body and thus accelerate the drug compound release time. The glycolide unit is, as is known, the most frequently used additional unit in polylactides.

The monomer molar ratio's of the lactide/glycolide units in the purified polymers according to the invention are preferably 100–25/0–75, particularly 75–25/25–75, especially 60–40/40–60, more especially 55–45/45–55, e.g. 55–50/45–50.

It is known that the polymerisation reaction of monomers like lactide and glycolide is preferably carried out in the presence of a compound having one or more hydroxylgroups, which functions as a starter in building up a linear polymer chain. Known starters are e.g. lactic acid and glycolid acid. Other hydroxyl group containing compounds can also be used, e.g. alcohols. The starters are in fact used to control the chain length of the polylactides. A smaller amount of starting hydroxyl compound leads to longer chains than greater amounts. Excellent regulators are polyols, e.g. those described in the UK Patent Application GB 2.145.422A, of which mannitol and especially glucose are the most preferred.

By using this type of starting compounds relatively high molecular weight hard polylactide-co-glycolide materials can be obtained, which are very suitable as implants or microparticle materials, and have 2 or 3, preferably more than 3, e.g. 4 relatively short polylactide-co-glycolide chains and can hydrolyse in the body tissues within a relatively short drug release period of some weeks to e.g. 2 months or more, preferably within 4–6, e.g. 5 weeks. Although according to the invention the purified polylactides can have a linear structure, the preferred purified polylactides according to the invention are those having the structure described in the GB Patent 2.145.422 A, being esters of a polyol containing at least 3 hydroxyl groups, preferably those being an ester of a sugar or a sugar alcohol, especially an ester of glucose. They are star shaped, having a centre of e.g. the glucose rest and rays of linear polylactide chains.

After their preparation the star polymers are, more than the linear polymers, contaminated by brown-coloured by-products, since the sugar or sugar alcohol, used for their preparation, is also be partially decomposed by the catalyst. The star polymers have monomer molar ratios of lactid/glycolide units which are preferably those, indicated above for the linear polymers.

The star polymers have preferably a mean molecule weight $M_w$ of from 10000 to 200000, especially of from 25000 to 100000, particularly of from 35000 to 60000, e.g. about 50000 and preferably have a polydipersity $M_w/M_n$ of from 1.7 to 3.0, especially from 2.0 to 2.5. Poly-lactide-co-glycolides of a linear structure, not being star polymers in a purified state according to the invention have preferably a mean molecular weight $M_w$ of from 25000 to 100000 and have preferably a polydispersity $M_w/M_n$ of from 1.2 to 2.

The molecular weight $M_w$ is determined by gelpermeation chromatography, using polystyrene as a standard, e.g. Dupont Ultrastyragel R 1000 or 500 Angstrom, in the column and e.g. tetrahydrofuron as the solvent.

The purified polylactides according to the invention can be obtained in a new process by contacting a solution of the impure polylactide with active charcoal and isolating the purified polylactide from the eluate. This process is also a part of the invention.

It is known from the UK Patent 1.467.970 and the EP 0181.621 A2 to treat polymers, produced in the presence of a catalyst with active charcoal.

According to the GB Patent 1.647.970, the polymer is a polyether, obtained from alkylene oxides, like ethylene oxide, propylene oxide or epichlorohydrin with an active hydrogen containing compound, e.g. glycerol, sorbitol or sucrose, in the presence of a basic catalyst. The polymer is purified with a mixture of active charcoal and magnesium silicate to remove crystals of polyalkylene glycols, e.g. polyethylene glycols, formed as by-products and which give the polymers a cloudy appearance and unsatisfactory viscosity and chemical properties. In a preferred method the polyethers are pretreated by means of a not further described other purification method to remove unreacted alkylene oxides and catalyst (page 2, lines 16–20). The basic catalyst thus could clearly not be removed by the charcoal—magnesium silicate mixture.

According to the EP 0181 621 A2 a solution of a polyalkylene ether in a cyclic ether or in a polyhydric alcohol solvent or the polyalkylene ether itself, e.g. polyoxytetramethylene glycol, prepared by the polymerisation of tetrahydrofuran under the influence of a heteropoly acid catalyst, e.g. 12-tungstophosphoric acid, is mixed with an organic hydrocarbon or halogenated hydrocarbon solvent. This solvent, which will contain the greatest part of the heteropoly acid, is separated from the other phase and the residue is contacted for further purification with a solid adsorbent, like charcoal, aluminium oxide or oxides, hydroxides or carbonates of e.g. Mg or Ca or with basic ion-exchange resins. According to Table 2 on page 23, the polymers contain 0.2 to 1.8 ppm of acidic metal contamination after purification with active charcoal.

This purification process is thus used to purify a polyether and to remove a very specific acidic catalyst type and it could not be foreseen, that active charcoal can be used for the removal of cations, like Sn++. Also it could not be foreseen, that such low impurity levels can be obtained as indicated.

The amounts of active charcoal used according to the purification process of the invention are generally from about 10 to 200%, e.g. 70 to 150% of the polymer weight. Any available charcoal can be used, e.g. as described in the Pharmacopoeia. A representative charcoal type is Norit of Clydesdate Co. Ltd., Glasgow/Scotland.

Typically powdered charcoal is used e.g. finely ground charcoal wherein at least 75% passes through a 75 micrometer sieve. Suitable charcoals as used in the Example hereafter, are described in brochures, available from Norit, e.g. "Summary of methods for testing Norit activated carbons on specifications" by J. Visser.

The new purification process with charcoal is especially of interest for star polymers which have a dark brown colour. The colour effect may partly be caused by the polyol, e.g. the glucose, being instable to heat, especially in the presence of a catalyst and is more pronounced than a reference solution of colour strength $B_1$.

It is believed that the presence of small amounts of acidic groups in the active charcoal are responsible for the surprisingly efficient removal of the cations. If a solution of the catalyst in an organic solvent is treated with charcoal, the catalyst compound is decomposed and the tin is removed with the charcoal, which is filtered of, whereas the anionic part of the catalyst is quantitatively found back in the remaining solution.

For this reason the invention also provides a method for the purification of the polylactide by contacting a solution of the impure polymer with a matrix having on its surface acidic groups and isolating the purified polylactide from the eluate.

If desired a weakly acidic cationic exchanger with a carboxylic acid functionality may be used if it is of an appropriately small particle size. For example, one with a hydrogen ionic form, a density when wet of about 0.69 g/ml (apparent) and 1.25 g/ml (true), a shipping weight of 690 g/liter, an effective particle size of 0.33 to 0.50 mm, a moisture content of 43 to 53 percent, a pH tolerated range of 5 to 14, a maximum operating temperature of 120° C., a total exchange capacity of 10 meq (dry) and 3.5 meq/ml (wet). An example is Amberlite IRC-50 Methacrylic aci DVB (available from Fluka, Switzerland) which is ground to have the particle size diameter reduced e.g. to below 1 mm or 100 microns.

The matrix for the purification, e.g. the charcoal, preferably has a suitable concentration of from 0.01 o 0.1 millimole of acidic groups per gram of matrix and is conveniently in the form of particles which may be finely divided. Typical particle diameters are e.g. from 1 micrometer to 1 mm, e.g. from 10 to 100 micrometers.

They have therefore a large surface area. For example active charcoal has a surface area of 1000 square metres for each ml of matrix substance.

The purification process of the invention is preferably related to a polylactide preparation using lactide and glycolide as monomers and metal cations, like $Sn^{++}$ as a catalyst, since this polymerisation process gives a better yield and, if desired, a higher molecular weight than the preparation process using lactid acid and glycolic acid as starting compounds and the strong acid ion-exchange resin as a catalyst, described in the European Patent No. 0026599.

Starting with an impure polylactide-co-glycolide containing about 1800 ppm of $Sn^{++}$, the concentration of $Sn^{++}$ can be lowered to about 200 ppm. A purification with charcoal can lower the $Sn^{++}$ content, as already mentioned, to less than 1.5, e.g. less than 1 ppm.

The purification process of the invention is preferably carried out with a solution of an impure polylactide in acetone although other solvents are possible.

The process may be followed by another purification process, preferably the process of ultrafiltration, which reduces the content of low molecular compounds, e.g. of lactide and glycolide. Also in this process a polylactide solution in acetone can be used.

After the second purification process purified polylactides can be obtained, having a monomer content of at most 1% by weight of polymer, preferable of at most 0.25% of polymer, e.g. of at most 0.2 % of lactide and 0.05% of glycolide, a water content of at most 1%, an organic solvent, e.g. methylene chloride or acetone, content of at most 1%, preferably of at most 0.5% e.g. of at most 0.3% and an ash content of at most 0.1% by weight of polylactide. Their acid number is preferable at most 10. The thus purified polylactides are preferably parenterally used, e.g. as a matrix for drug compounds, especially such in implants or in microparticles form. These forms may be prepared in conventional manners, which have abundantly been described in the literature e.g. in the European Application No 58481, the UK Patent Application GB 2.145.422, the European Patent Application No 52510 the U.S. Pat. Nos. 4,652,441 and 4,711,782, the French Application No 2.491.351, the U.S. Pat. No. 3,773,919.

The forms are suitable for e.g. incorporating a hydrophilic drug like a peptide, e.g. a cyclopeptide and particularly a hormonally active peptide, like a somatostatin, especially octreotide, or an acid addition salt or a derivative thereof, or a lipophilic drug, like an ergot alkaloid, e.g. bromocriptine.

The pharmaceutical compositions are formed by working up the purified polylactide with the drug compound to form an implantate or a microparticle.

EXAMPLE 1 a) Preparation of PLG-Glu

This is prepared as described in the above-mentioned UK Patent Application GB 2.145.422.

D,L-lactide and glycolide (60/40% by weight) containing trace amounts of lactic and glycolic acid as impurities, are polymerised at 130° in the presence of 0.2 percent (w/w) D (+) glucose and 0.6 percent (w/w) of tin octanoate (product T9 from M & T Chemicals which is the tin (II) salt of 2-ethyl hexanoic acid; Lemon yellow liquid; Viscosity (20° C.) 1.2636; Refractive Index 1.4950; Tin content 27–29%; 2-ethyl hexanoate content according to NaOH titration 69 percent).

The product is the polylactide-co-glycolide glucose ester (PLG-Glu) having a lactide/glycolide ratio of 60/40 g (basis) or 55/45 mole (basis). Mw=50000. Lactide/glycolide content ca 3% of weight. The colour is dark brown and is according to the used colour index more intensely coloured than a reference solution $B_1$. The tin content is 1800 ppm.

b) Treatment with Active Charcoal 130 g PLG-Glu is dissolved in 1950 ml acetone to give a clear dark brown solution. Within 5 minutes 130 g active charcoal is added. The mixture is stirred for 3 hours at room temperature and filtered. The material filtered off is washed with 1.5 litres of acetone. The filtrate is slightly yellow, of a colour index $B_9$. It is evaporated under a vacuum and the residue is dried at 70° C. and finally under a vacuum of 1 mm Hg. Mw=50000; Lactide/glycolide content ca 3%. Heavy metal content: less than 10 ppm.

Resultant analysis: Fe 3 ppm; Zn 1 ppm; Cu 1 ppm; Ni, Pb and Sn each under 1 ppm.

The filtered off charcoal contains practically all the tin and the filtrate practically all the 2-ethylhexanoic acid from the catalyst. (If the experiment is repeated with 50 percent active charcoal by weight of polymer then the product contains 290 ppm Sn)

c) Ultrafiltration

The product from step b) (180 g) is dissolved in 1.8 litres of acetone to give a bright yellow solution. The product is subjected to ultrafiltration using a laboratory pressure filtration apparatus, using acetone (ca. 4×1800 ml) as a solvent under a pressure of 5 bar having a membrane from DDS Type FS 81PP (exclusion limit 6000) diameter 14 cm, with a permeation rate of about 110 to 165 ml/hour. The permeation solution contains lactide/glycolide and lactic and glycolid acid and is coloured yellow. The residual solution in the pressure chamber (2215 ml of solution) is evaporated after a run of 46 hours. The product is taken up again in acetone, filtered and dried at 70 to 80° C. in a vacuum. The product (148 g) contains 0.2% by weight of lactide; 0.05% by weight of glycolide. Acetone content 0.3% by weight. No 2-ethyl hexanoic acid is detecable by gas chromatography (i.e. its content is less than 0.1 percent). $M_w$=50000 according to GPC.

Accordingly to the colour test laid down in the European Pharmacopoeia 2nd Edition, Section V.6.2 the polymer is "colourless". The product is not more intensely coloured than the reference solution $B_9$.

EXAMPLE 2

4 kg of poly(D,L-lactide-co-glycolide) purified according to the method of Example 1 and having a Mw 55100, were dissolved in 53 kg of methylene chloride.

To the filtered solution 1 kg of bromocriptine-mesylate was added. The resulting suspension was intensively mixed by means of an Ultra-Turrax and spray dried. The generated microparticles were sieved, washed with 0.01 molar methane-sulfonic acid/sodium chloride solution and rinsed with isotonic saline. The microparticles were dried under vacuum at 40–45° C. and sieved. The microparticles were filled in glass-vials under nitrogen and sterilized by gamma-irradiation (dose: 25 kGy).

The final product is an aseptically filled two chamber syringe (TCS) consisting of one compartment containing the microparticles and one compartment containing a vehicle for suspension of the microparticles.

| Vehicle composition: | |
| --- | --- |
| | mg/ml |
| Potassium-dihydrogenphosphate | 3.603 |
| Disodium-hydrogenphosphate (anhydrous) | 5.68 |
| Pluronic F68 | 2.0 |
| Sodium-carboxymethylcellulose (Blanose 7LFD) | 10.0 |
| Benzylalcohol | 10.0 |

| Vehicle composition: | |
|---|---|
| | mg/ml |
| Water for injections | ad 1.0 ml |
| Nitrogen | q.s. |

The TCS are suitable for e.g. i.m. administration, once every 4 weeks.

Results from clinical studies obtained with the TCS in postpartum women, patients with hyperprolactinemia/-microprolactinomas and patients with macroprolactinomas demonstrate a continuous release of active substance and a good systemic and local tolerability as well as good efficacy of single and multiple administrations of bromocriptine-microparticles.

EXAMPLE 3

One g of poly (D,L,-lactide-co-glycolide)glucose, $M_w$ 46000, (50/50) molar, (produced according to the process of GB 2.145.422, Polydispersity ca. 1.7, produced from 0.2% of weight glucose and purified according to Example 1) was dissolved in 10 ml of methylene chloride with magnetic stirring followed by the addition of 75 mg of Octreotide dissolved in 0.133 ml of methanol. The mixture was intensively mixed e.g. by means of an Ultra-Turax for one minute at 20,000 rpm causing a suspension of very small crystals of Octreotide in the polymer solution. The suspension was sprayed by means of a high speed turbine (Niro Atomizer) and the small droplets dried in a stream of warm air generating microparticles. The microparticles were collected by a "zyklon" and dryed overnight at room temperature in a vacuum oven.

The microparticles were washed with 1/15 molar acetate buffer pH 4.0 during 5 minutes and dried again at room temperature in a vacuum oven. After 72 hours the microparticles were sieved (0.125 mm mesh size) to obtain the final product.

The microparticles were suspended in a vehicle and administered i.m. in 5 mg/kg dose of Octreotide to white rabbits (chincillabastard) and s.c. in a 10 mg/kg dose to male rats.

Blood samples were taken periodically, indicating plasma levels of 0.3 to 10.0 ng/ml (5 mg dose) in rabbits and 0.5 to 7.0 ng/ml in rats for 42 days as measured by Radioimmunoassay (RIA) analysis.

What we claim is:

1. A purified linear polylactide polymer which is a linear polylactide-glycolide having a mean molecular weight Mw of from 46,000 to 60,000, a polydispersity $Mw/M_n$ of from 1.7 to 3.0, prepared by the process of polymerizing lactide and glycolide in the presence of tin di-(2-ethylhexanoate), followed by treatment with an amount of active charcoal equal to the weight of the polymer and ultrafiltration to yield a colorless or off-white product containing 1 to 1.5 parts per million $Sn^{++}$ residue.

2. The polylactide polymer of claim 1 having a lactidal glycolide molar ratio of 100–25/0–75.

3. The polylactide polymer of claim 1 having a lactide/glycolide molar ratio of 75–25/25–75.

4. The polylactide polymer of claim 1 having a lactide/glycolide molar ratio of 60–40/40–60.

* * * * *